United States Patent
van Bekkum et al.

(10) Patent No.: US 7,992,439 B2
(45) Date of Patent: Aug. 9, 2011

(54) ULTRASONIC PROBE HEAD

(75) Inventors: Aart Jan van Bekkum, Hoornaar (NL); Jeoren Martin van Klooster, Tiel (NL)

(73) Assignee: Krohne AG (CH)

( * ) Notice: Subject to any disclaimer, the term of this patent is extended or adjusted under 35 U.S.C. 154(b) by 287 days.

(21) Appl. No.: 12/206,796

(22) Filed: Sep. 9, 2008

(65) Prior Publication Data

US 2009/0071252 A1 Mar. 19, 2009

(30) Foreign Application Priority Data

Sep. 10, 2007 (DE) .......................... 10 2007 042 663

(51) Int. Cl.
*G01N 29/04* (2006.01)
(52) U.S. Cl. ........ 73/602; 73/1.15; 73/54.14; 73/861.25
(58) Field of Classification Search .................. 73/602, 73/1.15, 1.16, 54.14, 54.22, 817, 61.79, 61.49, 73/204.26, 861.25; 310/327, 334
See application file for complete search history.

(56) References Cited

U.S. PATENT DOCUMENTS

| | | | |
|---|---|---|---|
| 3,491,246 A * | 1/1970 | Doda et al. ................ | 250/231.19 |
| 3,955,484 A | 5/1976 | Hirahama et al. | |
| 4,746,831 A * | 5/1988 | Ichino ............................ | 310/334 |
| 5,029,474 A | 7/1991 | Schulze | |
| 5,747,672 A * | 5/1998 | Parent et al. ................... | 73/61.79 |
| 6,400,648 B1 | 6/2002 | Heijnsdijk et al. | |
| 6,437,482 B1 * | 8/2002 | Shibata .......................... | 310/320 |
| 7,416,029 B2 * | 8/2008 | Telfer et al. .................... | 166/386 |

FOREIGN PATENT DOCUMENTS

| | | |
|---|---|---|
| DE | 3303412 C2 | 11/1984 |
| DE | 100 21 187 C1 | 5/2001 |
| DE | 102005044880 A1 | 5/2007 |
| EP | 0108852 | 5/1984 |
| JP | 2005077118 * | 3/2005 |
| WO | WO 2006/061329 A2 | 6/2006 |

* cited by examiner

*Primary Examiner* — Jacques M Saint Surin
(74) *Attorney, Agent, or Firm* — Cesari and McKenna, LLP; John F. McKenna

(57) ABSTRACT

An ultrasonic probe head, in particular for an ultrasonic flow meter having a housing and an ultrasonic transducer in the housing, wherein ultrasonic signals can be created and/or detected by the ultrasonic transducer and the ultrasonic signals from the ultrasonic transducer can be emitted and/or received via an ultrasonic window. A thin, relatively flexible solid interface layer is provided between the ultrasonic transducer and the ultrasonic window, the surface of the ultrasonic window having contact with the solid interface layer has a specified roughness and the ultrasonic transducer is impacted with a force, wherein the material of the solid interface layer and the ultrasonic window, the specified roughness of the surface of the ultrasonic window and the force are attuned to one another so that the solid interface layer nestles into the ultrasonic window of the housing at least also by plastic deformation. Thus, a passage is created between the ultrasonic transducer and the ultrasonic window that eliminates, at least partially, the known disadvantages between the ultrasonic transducer and the ultrasonic window.

13 Claims, 1 Drawing Sheet

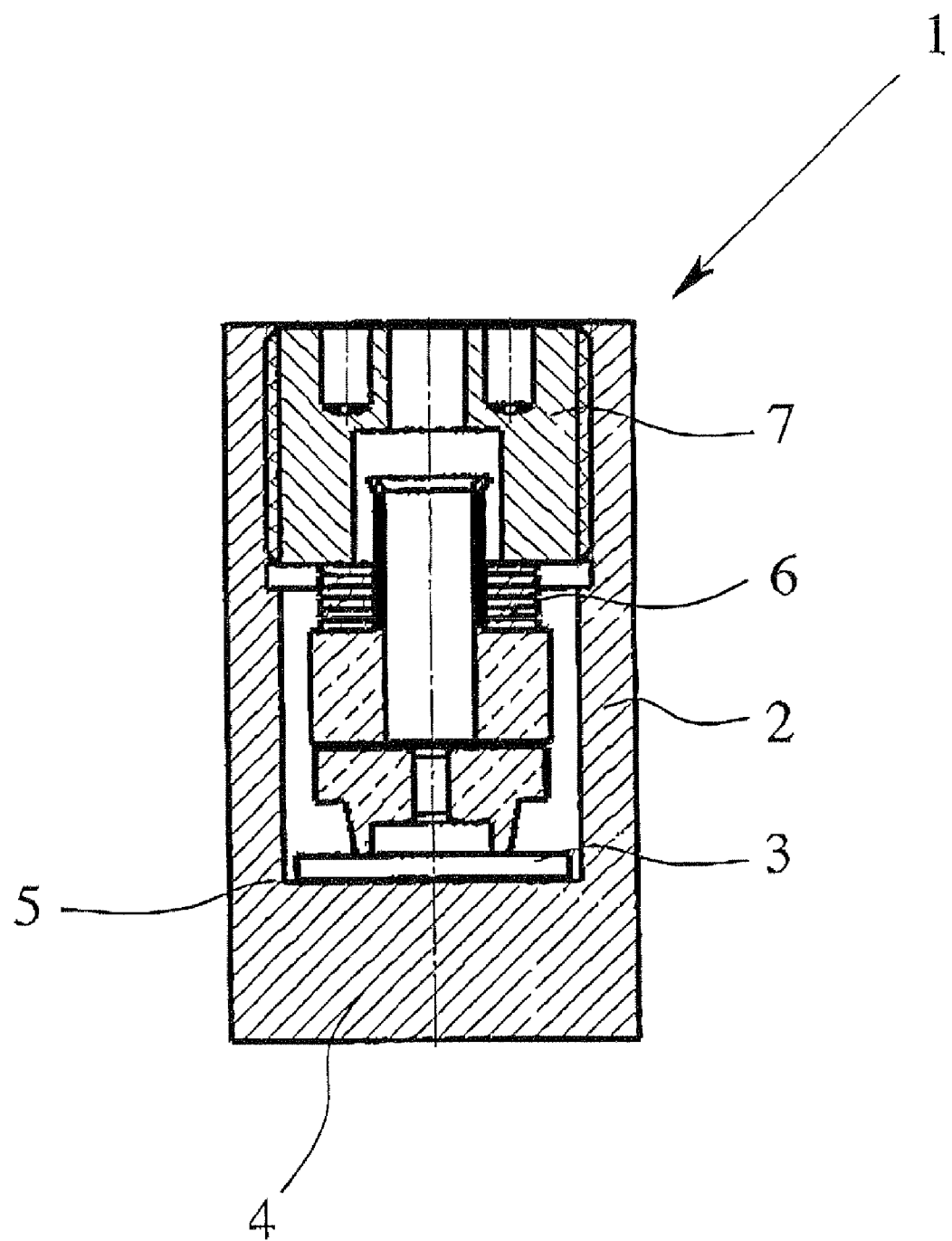

ULTRASONIC PROBE HEAD

The invention relates to an ultrasonic probe head, in particular for an ultrasonic flow meter having a housing and an ultrasonic transducer arranged in the housing, wherein ultrasonic signals can be created and/or detected by the ultrasonic transducer and the ultrasonic signals from the ultrasonic transducer can be emitted and/or received via an ultrasonic window.

BACKGROUND OF THE INVENTION

1. Field of the Invention

Ultrasonic probe heads of this kind have been known for a long time and are used, for example, in the field of process engineering in ultrasonic flow meters, wherein, in this case, the use of the ultrasonic probe head is not of importance, and the subsequently described teaching of the invention can, moreover, be used by a plurality of different ultrasonic probe heads.

In the ultrasonic probe head in question, a preferably good connection between the ultrasonic transducer and the ultrasonic window of the housing is decisive, wherein "a preferably good" connection means that the contact surface formed, on the one hand, by the surface of the ultrasonic transducer and, on the other hand, by the surface of the ultrasonic window is preferably large so that the ultrasonic signals emitted by the ultrasonic transducer or, respectively to be received, can pass, preferably unobstructed, over the previously-mentioned contact surface. When the contact surface is only inadequately formed and air pockets exist between the ultrasonic transducer and the ultrasonic window, the acoustic interface between the ultrasonic transducer and the ultrasonic window is limited, since the ultrasonic signals are practically reflected at the boundary layer to air and, thus, cannot conversely exchange from the ultrasonic transducer to the ultrasonic window.

2. The Prior Art

It is known from the prior art to glue the ultrasonic transducer and the ultrasonic window to one another with an adhesive. The problem with this is that the known and used adhesives often have only a marginal resistance to heat exposure and, among other things, gasify under heat exposure with the result that gas pockets are formed within the adhesive having undesired boundary layers; this implicates the negative effects for the transmission ability of the ultrasonic signals described above. Additionally, it is disadvantageous that the ultrasonic transducer can disconnect entirely from the ultrasonic window or, respectively, the housing due to the diminished stability of the adhesive under heat exposure. Furthermore, it has been seen that adhesives also lose their effectiveness at very low temperatures, as e.g. in so-called cryogenic applications, so that ultrasonic probe heads having a glued ultrasonic transducer are presently only able to be used in a limited range of temperatures from about −40° C. to about +150° C.

It is also known from the prior art to make a moist interface between the ultrasonic transducer and the ultrasonic window of the housing, for example by using liquids having an oil base. The same occurrences apply for high and low temperature applications with such moist interfaces as in the abovementioned glued interface. The liquids used are unstable at high temperatures, e.g. they may gasify, and lose their connecting effectiveness at very low temperatures.

It is known from DE 100 21 187 C1 to make an ultrasonic probe head usable for high and low temperature applications by thermally insulating the ultrasonic transducer using an ultrasonic waveguide and thus also the interface from the ultrasonic transducer and ultrasonic waveguide. However, using an ultrasonic waveguide is disadvantageous in that an additional signal propagation delay has to be taken into consideration, which entails an additional uncertainty of measurement. In particular, in low temperature applications, an undesired heat input in the measuring media can occur via the ultrasonic waveguide which may lead to a change of the media that can seriously affect measurement. For example, contact with liquid nitrogen, which has a boiling point of about −196° C. at atmospheric pressure, can quickly lead to the formation of bubbles on the end of the ultrasonic window or, respectively the ultrasonic waveguide facing the media, which, once again, substantially limits transmission of the ultrasonic signal.

SUMMARY OF THE INVENTION

The object of the present invention is to eliminate, at least partially, the described disadvantages in the known ultrasonic probe heads of the type in question.

The ultrasonic probe head according to the invention, in which the object derived and described above is solved, is first and essentially characterized in that a thin, relatively flexible solid interface layer is provided between the ultrasonic transducer and the ultrasonic window of the housing, that the surface of the ultrasonic window having contact with the solid interface layer has a specified roughness and the ultrasonic transducer is impacted with a force, wherein the material of the solid interface layer and the ultrasonic window, the specified roughness of the surface of the ultrasonic window and the force are attuned to one another so that the solid interface layer nestles into the ultrasonic window of the housing at least also by plastic deformation.

Solely based on the fact that the ultrasonic transducer is impacted with the force, the thin, relatively flexible solid interface layer is affixed as communicating media between the ultrasonic transducer and the surface of the ultrasonic window on the inside of the housing, so that, in choosing an appropriate material for the solid interface layer, the known temperature sensitivity of adhesive interfaces or also of liquid interfaces between the ultrasonic transducer and the surface of the ultrasonic window can be avoided. However, this measure alone cannot guarantee that the contact surface formed between the solid interface layer and the surface of the ultrasonic window is actually as large as possible and, thus, particularly well-suited for ultrasonic transmission, the remaining solid air surfaces, i.e. passage from the solid interface layer to air or from the surface of the ultrasonic window to air, are made as small as possible.

According to findings known from the prior art about the formation of the contact surfaces between two boundary layers that consist of different substances with different material properties (modulus of elasticity, hardness) and geometrical surface characteristics (roughness), the tendency of forming a contact surface between such materials can be expressed, e.g. using the plasticity ratio ψ. The plasticity ratio ψ can, for example, be defined, according to a common model for the contact between rough surfaces, by:

$$\psi = \frac{2E}{\pi K H} \cdot \sqrt{\frac{\sigma_s}{R}} \qquad (1)$$

In the definition of the plasticity ratio ψ described above, E is the module of elasticity, K is the hardness constant, which is dependent on Poisson's ratio of the more flexible material, H is the hardness of the more flexible material, R is the radius of curvature of surface irregularities and $\sigma_S$ describes the standard deviation of the surface irregularities. For a detailed description of the ratio given above, the following article from Kogut, L. et al shall be referred to as an example: "An improved elastic-plastic model for the contact of rough surfaces", 3rd Aimeter International Tribology Conference, 2002.

The plasticity ratio $\psi$ is described using a first term that is dependent only on material factors, namely the parameters E, K and H and using a second term that is dependent only on geometric surface ratios, namely $\sigma_S$ and R. The combination of surfaces that are formed of materials with specific material factors and that have specific geometric surface characteristics to a contact surface, is described by the plasticity ratio $\psi$ to the effect that it represents the relation of the attained contact surfaces between both surfaces at a specific force, at which these surfaces are pressed against one another.

In a surface combination having a small plasticity ratio $\psi$, the attained contact surface increases immensely with an increase in the force at which the surfaces are pressed against one another, whereas in surface combinations having a larger plasticity ratio $\psi$, the actual contact surface between the surfaces only increases slightly at the same increase of the force at which the surfaces are pressed against one another. For values higher than 8 of the plasticity ratio, the contact between the surfaces becomes completely plastic and independent of the plasticity ratio.

When the relation described above is followed, to attain a preferably large contact surface between two surfaces—here, i.e., the surface of the solid interface layer and the ultrasonic window—at a specified—i.e. initially arbitrary, then constant—force on these surfaces, the plasticity ratio must be set as small as possible, i.e. a choice of substances having a module of elasticity as small as possible, on the one hand, and on the other hand, a hardness as great as possible as well as a preferably small roughness of the surface, i.e. with a standard deviation of surface irregularities as small as possible and a radius of curvature of surface irregularities as large as possible. Applicable to the case at hand, the surface of the ultrasonic window on the inside of the housing must be as smooth as possible and the material of the solid interface layer must have an elasticity that is as low as possible.

However, according to the teaching of the invention, it has been seen that a greater contact surface and, thus, a better ability for ultrasonic transmission is realized between the solid interface layer and the surface of the ultrasonic window, when the surface of the ultrasonic window on the inside of the housing does not have the smallest possible roughness, but rather a specific roughness. This roughness, i.e. the occurrence of particular irregularities of the surface of the ultrasonic window, which is usually produced on a stiffer material than the thin, relatively flexible solid interface layer, entails that pointed irregularities of the surface of the ultrasonic window lead to stresses in the solid interface layer at a specific force, which lie above the yield point of the relatively flexible solid interface layer, so that the relatively flexible solid interface layer can conform to the irregularities of the ultrasonic window using plastic deformation, and so that the solid interface layer, also at least using plastic deformation, is nestled onto the ultrasonic window of the housing.

The maximum force exertable on the ultrasonic transducer is defined by the stiffness of the material of the ultrasonic transducer; the maximum force exerted on the ultrasonic transducer may only lead to stresses within the ultrasonic transducer that lie below the destruction limit of the material used for the ultrasonic transducer, wherein the ultrasonic transducer normally consists of a piezo-crystal. In predetermined materials for the solid interface layer and the normally harder ultrasonic window, the surface of the ultrasonic window is provided with a roughness that does not, according to the teaching known from the prior art, attain a minimum value, but rather a predetermined, greater value according to the invention, which leads to a greater contact surface between the solid interface layer and the surface of the ultrasonic window.

Under consideration of all of these basic conditions, the plasticity ratio $\psi$ of the contact surface between the ultrasonic transducer and the ultrasonic window of the housing lies in a preferred embodiment of the invention in the range [0 . . . 8], i.e. in a range in which the attained contact surface between the two surfaces changes at a predetermined force impact still with a change of the plasticity ratio.

According to a further preferred embodiment of the invention, the plasticity ratio $\psi$ of the contact surface between the ultrasonic transducer and the ultrasonic window of the housing is as small as possible, wherein this is attained, in particular with a low roughness of the surface of the ultrasonic window, in particular with a small standard deviation and/or due to a large radius of curvature of the irregularities of the surface of the ultrasonic window. However, it should be taken into consideration here that the roughness can not be reduced arbitrarily, since, according to the invention, a certain minimum roughness needs to remain in order to guarantee a maximum contact surface and, thus, the best possible ultrasonic transmission.

According to a further preferred embodiment of the invention, the contact surface between the solid interface layer and the ultrasonic window of the housing is as large as possible, particularly preferred at maximum, due to the plastic deformation of the solid interface layer attained with the predetermined force impact. Not only is a larger contact surface attained than is possible in an embodiment of the surfaces according to the prior art (firm surface "as smooth as possible", opposing material "as flexible as possible"), but also an optimum design of the contact surfaces between both surfaces.

According to a further, particularly advantageous embodiment of the invention, the solid interface layer consists of a material that remains "solid" in a temperature range of between for instance −200° C. and +300° C., which corresponds to a temperature range in which the known interface layers of adhesives or liquids fails in view of transmission of ultrasonic signals between the ultrasonic transducer and the ultrasonic window of the housing. In this context, it has been shown to be particularly advantageous when the solid interface layer consists of metal or a metal alloy, in particular of silver, gold or platinum, wherein gold is, all in all, particularly suitable for attaining a good contact surface for transmitting ultrasonic signals.

According to a further preferred embodiment of the invention, the solid interface layer is thinner than about a tenth of the wavelength of the ultrasonic signal to be transmitted in the direction of dispersion, wherein a loss of energy is very low from transmission of the ultrasonic signal via the solid interface layer and is of almost no consequence for signal transmission.

In detail, there are different possibilities of embodying and further developing the ultrasonic probe head according to the invention. The dependent claims and the description of a preferred embodiment in connection with the drawing should be referred to in this case.

BRIEF DESCRIPTION OF THE DRAWINGS

The only drawing FIGURE shows an embodiment of an ultrasonic probe.

DESCRIPTION OF A PREFERRED EMBODIMENT

As shown in the drawing, the probe includes a head 1 having a housing 2 and a ultrasonic transducer 3 arranged in the housing 2, wherein ultrasonic signals can be created and/or detected by the ultrasonic transducer 3 and the ultrasonic signals from the ultrasonic transducer 3 can be emitted and/or received via an ultrasonic window 4. The ultrasonic window 4 of the housing 2 is simply the area of the housing 2 by way of which the ultrasonic signal is transmitted from the housing 2 into the neighboring (not shown here) media. The ultrasonic window 4 does not have to be designed of a particular substance or in a particular geometric manner, rather can simply exist—as in the embodiment shown—in the geometric connecting passage between the ultrasonic transducer 3 and the media adjacent the housing 2. In the illustrated ultrasonic probe head 1, a thin, relatively flexible solid interface layer 5 is provided between the ultrasonic transducer 3 and the ultrasonic window 4 of the housing 2. The surface of the ultrasonic window 4 in contact with the solid interface layer 5 has a predetermined roughness and the ultrasonic transducer 3 is applied with a force so that the ultrasonic transducer 3 presses the solid interface layer 5 onto the inside of the housing of the ultrasonic window 4.

The materials of the solid interface layer 5 and the ultrasonic window 4, the predetermined roughness of the surface of the ultrasonic window 4 and the force that is applied on the ultrasonic transducer 3 are attuned to one another so that the solid interface layer 5 at least also using plastic deformation is nestled against the ultrasonic window 4 of the housing 2.

As opposed to the dry interface between the ultrasonic transducer 3 and the ultrasonic window 4 known from the prior art, the roughness of the surface of the ultrasonic window 4 is not designed as small as possible, but is provided with a predetermined roughness, which guarantees that, at the predetermined force at which the ultrasonic transducer 3 is applied, the solid interface layer 5 is nestled against the ultrasonic window 4 of the housing 2, at least also using plastic deformation, wherein a greater contact surface can be made between the ultrasonic transducer 3 and the ultrasonic window 4 than between surfaces of the ultrasonic window 4 of the housing 2 with surfaces that are as smooth as possible. This is based on the fact that a certain roughness of the surface of the ultrasonic window 4 is necessary in order to create a mechanical stress within the solid interface layer 5 at a predetermined force, which lies above the yield point of the material from which the solid interface layer 5 is produced.

In the ultrasonic probe head shown, the plasticity ratio $\psi$ of the contact surface described above between the ultrasonic transducer 3 and the ultrasonic window 4 of the housing lies at about 1, thus within the range [0 . . . 8].

In the embodiment shown, the plasticity ratio $\psi$ of the contact surface between the ultrasonic transducer 3 and the ultrasonic window 4 of the housing 2 is configured as small as possible, namely in that the standard deviation $\sigma_S$ of the irregularities of the surface of the ultrasonic transducer 3 are made as small as possible, which means that the heights of the irregularities are close together in terms of value and only deviate from one another in a small range. In other embodiments not shown here, a plasticity ratio $\psi$ that is as small as possible is attained in that the radius of curvature R of the surface irregularities of the ultrasonic window 4 are made as large as possible, wherein the roughness in total may not be lowered so far that the surface irregularities are no longer capable of plastically deforming the solid interface layer in any case.

In total, in choosing the material for the thin, relatively flexible solid interface layer 5, the roughness of the surface of the ultrasonic window 4 and the force that presses the ultrasonic transducer 3 on the solid interface layer 5 are taken into consideration, so that the force does not lead to a destruction of the ultrasonic transducer 3, which is a piezo-crystal in the case shown. Further, it must be taken into consideration that though it is advantageous to have a plasticity ratio $\psi$ that is as small as possible of the contact surface between the ultrasonic transducer 3 and the ultrasonic window 4 of the housing 2, the roughness of the surface of the ultrasonic window 4 may not be lowered so far that plastic deformation of the flexible solid interface layer 5, in particular in a microscopic scale, is no longer possible.

In the embodiment shown, the solid interface layer 5 is made of gold, which ensures that the solid interface layer 5 remains "solid" in the aggregate state at a temperature range between, for instance, −200° C. and +300° C., wherein gold, as it is known, remains in this aggregate state at temperatures far in excess of 300° C. It is thus achieved by the embodiment shown of the ultrasonic probe head 1 that a larger contact surface is formed between the ultrasonic transducer 3 and the surface of the ultrasonic window 4 than in the known design of the surface area, wherein furthermore, the disadvantages of the known adhesive or liquid interface layers are avoided as are measurement uncertainties that are intrinsically tied to the use of ultrasonic waveguides.

Furthermore, in the embodiment shown, the solid interface layer 5 is thinner than one tenth of the wavelength of the ultrasonic signal to be transmitted in the direction of transmission of the ultrasonic signal, which guarantees that the loss of energy of the ultrasonic signal to be transmitted is only very low.

In the illustrated ultrasonic probe head 1, the force that is applied on the ultrasonic transducer 3 is created by a spring element 6, wherein the spring element 6 consists presently of a plurality of disk springs. A certain tolerance against thermal expansion of the arrangement is achieved by this measure. The spring element 6 is pre-compressible in the embodiment shown, namely using a screwing element 7 that can be screwed into the housing 2 of the ultrasonic probe head 1, and which presses on the spring element 6.

REFERENCE NUMBERS 1. ultrasonic probe head
2. housing
3. ultrasonic transducer
4. ultrasonic window
5. solid interface layer
6. spring element
7. screwing element

What is claimed is:

1. An ultrasonic probe head, in particular for an ultrasonic flow meter having a housing and an ultrasonic transducer arranged in the housing, wherein ultrasonic signals are created and/or detected by the ultrasonic transducer and the ultrasonic signals from the ultrasonic transducer are emitted and/or received via an ultrasonic window, and wherein a thin, relatively flexible solid interface layer is provided between the ultrasonic transducer and the ultrasonic window of the housing, a contact surface of the ultrasonic window having contact with the solid interface layer has a specified roughness and the ultrasonic transducer is impacted with a force, the improvement wherein the material of the solid interface layer and the ultrasonic window, the specified roughness of a contact surface of the ultrasonic window and the force are attuned to one another so that the solid interface layer nestles into the ultrasonic window of the housing at least also by plastic deformation and wherein the contact surface between the solid interface layer and the ultrasonic window of the housing is as large as possible, in particular a maximum due to the plastic deformation of the solid interface layer.

2. The ultrasonic probe head according to claim 1, wherein the plasticity ratio ($\psi$) of said contact surface between the ultrasonic transducer and the ultrasonic window of the housing lies within the range [0 . . . 8].

3. The ultrasonic probe head according to claim 1, wherein the plasticity ratio ($\psi$) of said contact surface is as small as possible, in particular due to a small standard deviation $\sigma_S$ and/or due to large radii of curvature (R) of the irregularities of the surface of the ultrasonic window.

4. The ultrasonic probe head according to claim 1, wherein the plasticity ratio ($\psi$) of the contact surface between the ultrasonic transducer and the ultrasonic window of the housing lies within the range [0 . . . 8] and is as small as possible, in particular due to a small standard deviation $\sigma_S$ and/or due to large radii of curvature (R) of the irregularities of the surface of the ultrasonic window.

5. The ultrasonic probe head according to claim 1, wherein the solid interface layer is "solid" in the aggregate state at a temperature range of between −200° C. and +300° C.

6. The ultrasonic probe head according to claim 1, wherein the plasticity ratio ($\psi$) of the contact surface described above between the ultrasonic transducer and the ultrasonic window of the housing lies within the range [0 . . . 8] and the solid interface layer is "solid" in the aggregate state at a temperature range of between −200° C. and +300° C.

7. The ultrasonic probe head according to claim 1, wherein the plasticity ratio ($\psi$) of the contact surface is as small as possible, in particular due to a small standard deviation $\sigma_S$ and/or due to large radii of curvature (R) of the irregularities of the surface of the ultrasonic window and the solid interface layer is "solid" in the aggregate state at a temperature range of between −200° C. and +300° C.

8. The ultrasonic probe head according to claim 1, wherein the solid interface layer is made of metal or a metal alloy, in particular of silver, gold or platinum.

9. The ultrasonic probe head according to claim 1, wherein the plasticity ratio ($\psi$) of the contact surface between the ultrasonic transducer and the ultrasonic window of the housing lies within the range [0 . . . 8] and the solid interface layer is made of metal or a metal alloy, in particular of silver, gold or platinum.

10. The ultrasonic probe head according to claim 1, wherein, in the direction of dispersion, the solid interface layer is thinner than one tenth of the wavelength of the ultrasonic signal to be transmitted.

11. The ultrasonic probe head according to claim 1, wherein said force can be created by a spring element, wherein the spring element consists preferably of a plurality of disk springs.

12. The ultrasonic probe head according to claim 11, wherein said force is created by a spring element, wherein the spring element consists preferably of a plurality of disk springs and that the spring element is pre-compressible, in particular by a screwing element that is screwed into the housing of the ultrasonic probe head.

13. The ultrasonic probe head according to claim 1, wherein the plasticity ratio ($\psi$) of the contact surface is as small as possible, in particular due to a small standard deviation $\sigma_S$ and/or due to large radii of curvature (R) of the irregularities of the surface of the ultrasonic window and said force is created by a spring element, wherein the spring element consists preferably of a plurality of disk springs and the spring element is pre-compressible, in particular by a screwing element that is screwed into the housing of the ultrasonic probe head.

* * * * *